United States Patent [19]

Hofmann

[11] Patent Number: Plant 5,311

[45] Date of Patent: Oct. 30, 1984

[54] VARIETY OF GERANIUM NAMED 'ALEX'

[75] Inventor: Guenter Hofmann, Dresden, German Democratic Rep.

[73] Assignee: Oglevee Associates, Inc., Connellsville, Pa.

[21] Appl. No.: 477,922

[22] Filed: Mar. 23, 1983

[51] Int. Cl.[3] ..... A01H 5/00

[52] U.S. Cl. ..... Plt./68

[58] Field of Search ..... Plt./68

*Primary Examiner*—James R. Feyrer

*Attorney, Agent, or Firm*—Webb, Burden, Robinson & Webb

[57] ABSTRACT

A new geranium cultivar is distinguished by its brilliant color, short and compact plant, more basil branching, close internodes, small leaves and short flower stems with the flowers positioned immediately atop the foliage. The new cultivar further provides early flowering and is more floriferous as compared with commonly grown zonal geraniums.

3 Drawing Figures

BACKGROUND OF THE NEW PLANT

The present invention comprises a new and distinct cultivar of *Pelargonium hortorum,* Bailey known by the varietal name of Alex. The new variety was discovered in a selective breeding program and is a seedling resulting from the cross of the seed parent Dresdner Rubin Selection X Walter Dietzmann and the pollen parent Dresdner Rubin Selection.

The new cultivar was discovered in the year 1973 in Dresden, German Democratic Republic; was first asexually reproduced by cuttings in Dresden, German Democratic Republic and has been repeatedly asexually reproduced by cuttings at Oglevee Floral Company in Connellsville, Pa. over an eighteen month period. It has also been trialed and field tested at Connellsville during the summers of 1981 and 1982. It has been found to retain its distinctive characteristics through successive propagations.

The new cultivar, when grown in a greenhouse in Connellsville, Pa., using natural light and 62° F. night temperature and 70° F. day temperature, has a response time of five weeks from a well rooted cutting to a flowering plant in a four inch (10 cms.) pot.

DESCRIPTION OF THE DRAWING

FIG. 1 is a graph of the flavonols fingerprinting,

DESCRIPTION OF THE NEW PLANT

Figure 1:
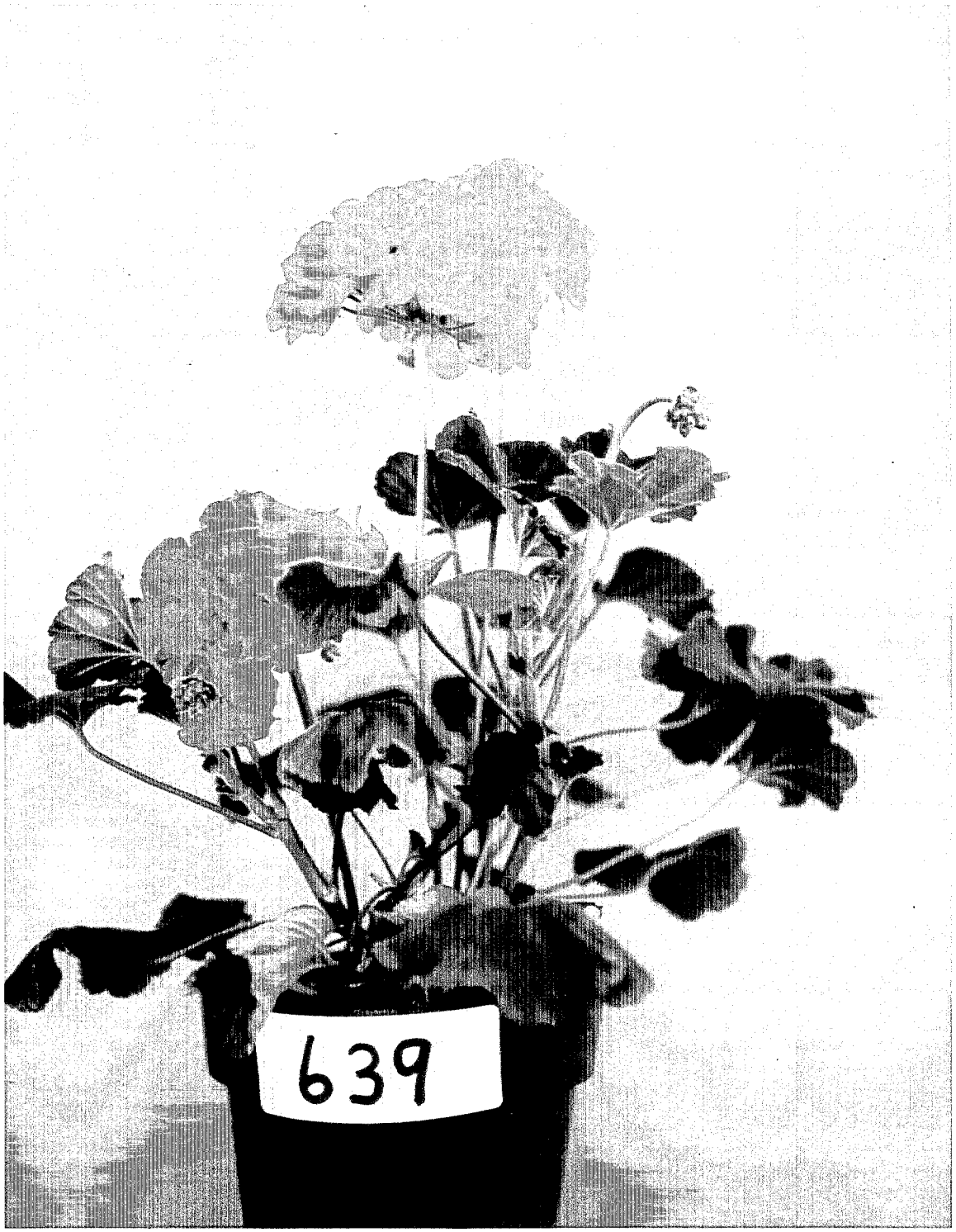
FIG. 1 of the accompanying photographic drawing illustrates the new cultivar, the color being as nearly true as possible with color illustrations of this type.

The following detailed descriptions set forth the characteristics of the cultivar. The data which define these characteristics were collected from asexual reproductions carried out by the Oglevee Floral Company in Connellsville, Pa. The plant history was taken on five week plants, blossomed under natural light in a greenhouse and color readings were taken indoors under 100 foot candles of cool, white florescent light. Color references are primarily to the R.H.S. Colour Chart of The Royal Horticultural Society of London.

THE PLANT

Classiffication:

*Botanical.*—*Pelargonium hortorum,* Bailey.

*Commercial.*—Zonal geranium.

Form: Bush.

Height: 12 To 18 cms. (15 cms. average) as a four inch pot plant excluding bloom and 22 to 28 cms. (25 cms. average) as a four inch pot plant including bloom.

Growth: Short and compact with more basil branching, closer internodes and smaller leaves as compared with commonly grown zonal geraniums.

Strength: Very sturdy with a low susceptibility to wind and rain damage.

Foliage: The quantity of foliage is of below average abundance.

Leaves:

*Size.*—7.5 To 10 cms. across.

*Shape.*—Reniform with oblique base.

*Margin.*—Cuneate.

*Texture.*—Leathery and pubescent.

*Color.*—Upperside — Fan 3 Green Group 137A; Underside — Fan 3 Green Group 138B.

*Ribs and veins.*—Palmate.

Petioles: 7 To 10 cms.

Stem:

*Color.*—Fan 3 Yellow Green Group 144A.

*Internodes.*—1 To 2 cms. in length.

THE BUD

Shape: Umbel formed with approximately 50 florets.

Size: As bud develops at first color show, head size is $2\frac{3}{4}$ cms. and it opens into a fully developed head size of 10 to 11 cms. in diameter.

INFLORESCENCE

Blooming habit: Continuous throughout the year.

Size: 10 to 11 cms. across.

Borne: Singly in an umbel form.

Florets:

*Form.*—Flat to slightly cupped; non-symmetrical and irregular in shape.

*Petals.*—6 To 7 in number, plus 3 petaloids; upperside overall, Fan 1 Red Group 40A; base of the 2 upper petals, Fan 2 Red Purple Group 58C; underside, Fan 1 Red Group 40C.

*Size.*—Fairly large, 5 to 5.5 cms. across.

*Texture and appearance.*—Firm and satiny.

Petaloids:

*Quantity.*—5 To 6 in number.

*Shape.*—Small and twisted.

*Color.*—Same as Florets.

Pedicel: Length 2 cms.

Peduncle: Length 12 to 18 cms.

Persistance: Nonshattering flower.

Disease resistance: Better than average to Botrytis.

Lasting quality: On the order of three weeks.

REPRODUCTIVE ORGANS

Stamens:

*Anthers.*—Imperfectly formed on flattened filaments; resemble petaloids 2 to 6 in number.

*Filaments.*—Streaked white and red to red; growing together with petaloids, 6 in number; nonuniform; 0.5 to 1 cm. in length.

*Pollen.*—Golden yellow, very little pollen.

Pistils:

*Number.*—1.

*Length.*—1 cm.

*Stigma.*—5 Arms upright, reddish purple in color, similar to base of petal.

*Style.*—Reddish purple.

Ovaries: Green, 5 carpels.

Fruit: Nonfertile.

The following evaluation is a result of the trialing and field testing carried out in the summer of 1982 at Connellsville, Pa. and compares the new geranium cultivar to the standard cultivar "Irene" presently commercialized in the United States. The ratings are taken on plants planted in June and evaluated at three different times throughout the summer. The plants were evaluated as to height, flowering, number of flowers, heat tolerance and form. The rating is based on a weighted average. A rating of 1.0 is poor and a rating of 10.0 is outstanding.

| CULTIVARS | EVALUATIONS 7/13/82 | 8/15/82 | 9/15/82 | AVERAGE SEASONAL RATING |
|---|---|---|---|---|
| ALEX | 7.0 | 7.0 | 8.0 | 7.3 |
| IRENE | 7.0 | 6.0 | 6.0 | 6.7 |

The new cultivar is characterized by its brilliant color and its short and compact plant. There is more basil branching and close internodes and small leaves as compared with the standard bush zonal geraniums produced in the United States. A short flower stem positions the flower immediately atop of the foliage into the plant and renders the plant very resistant to wind and rain damage. The plants provide early flowering and are more floriforous as compared to the standard United States varieties.

Figure 2:
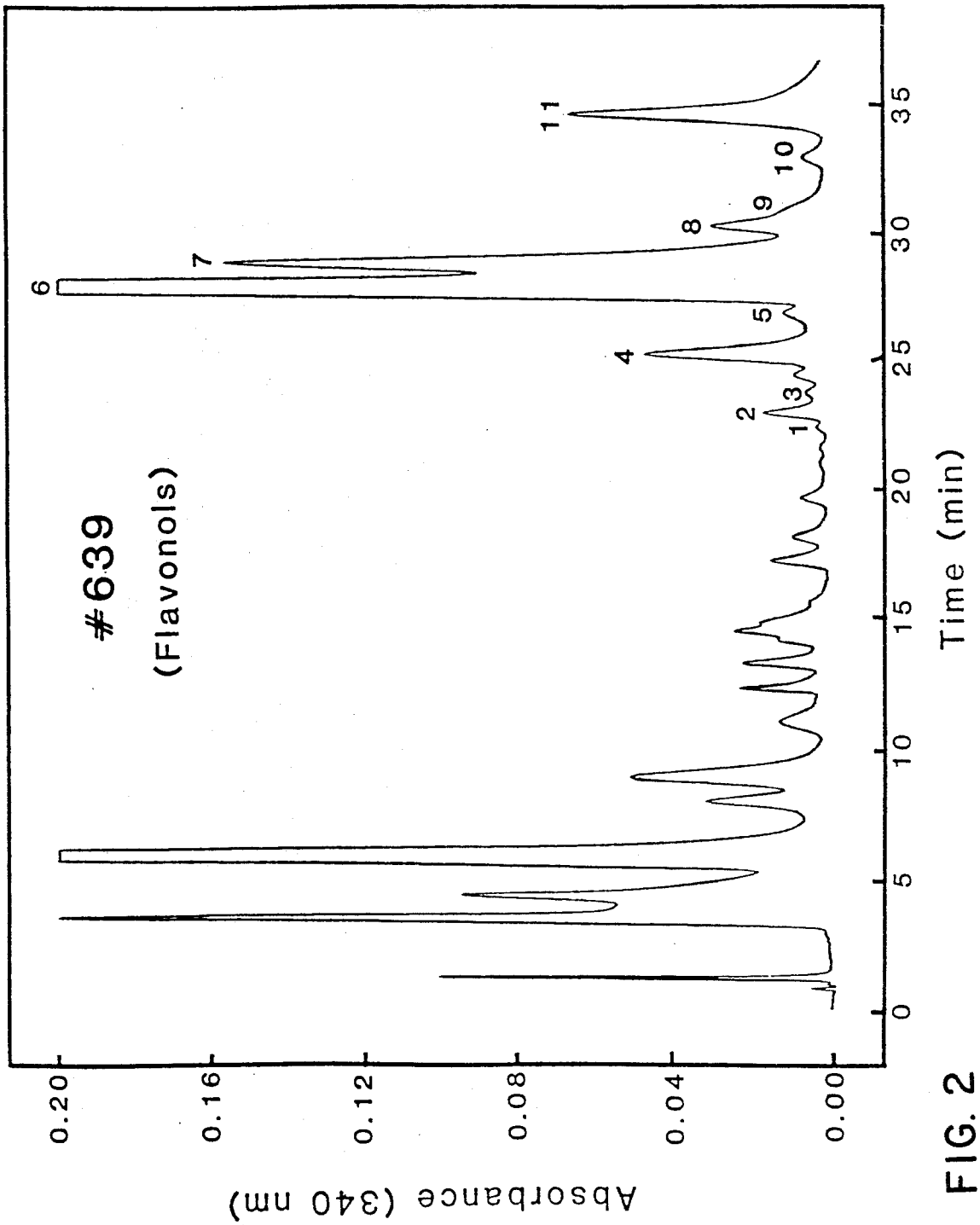
FIG. 2 is a graph of flavonols fingerprinting.
Figure 3:
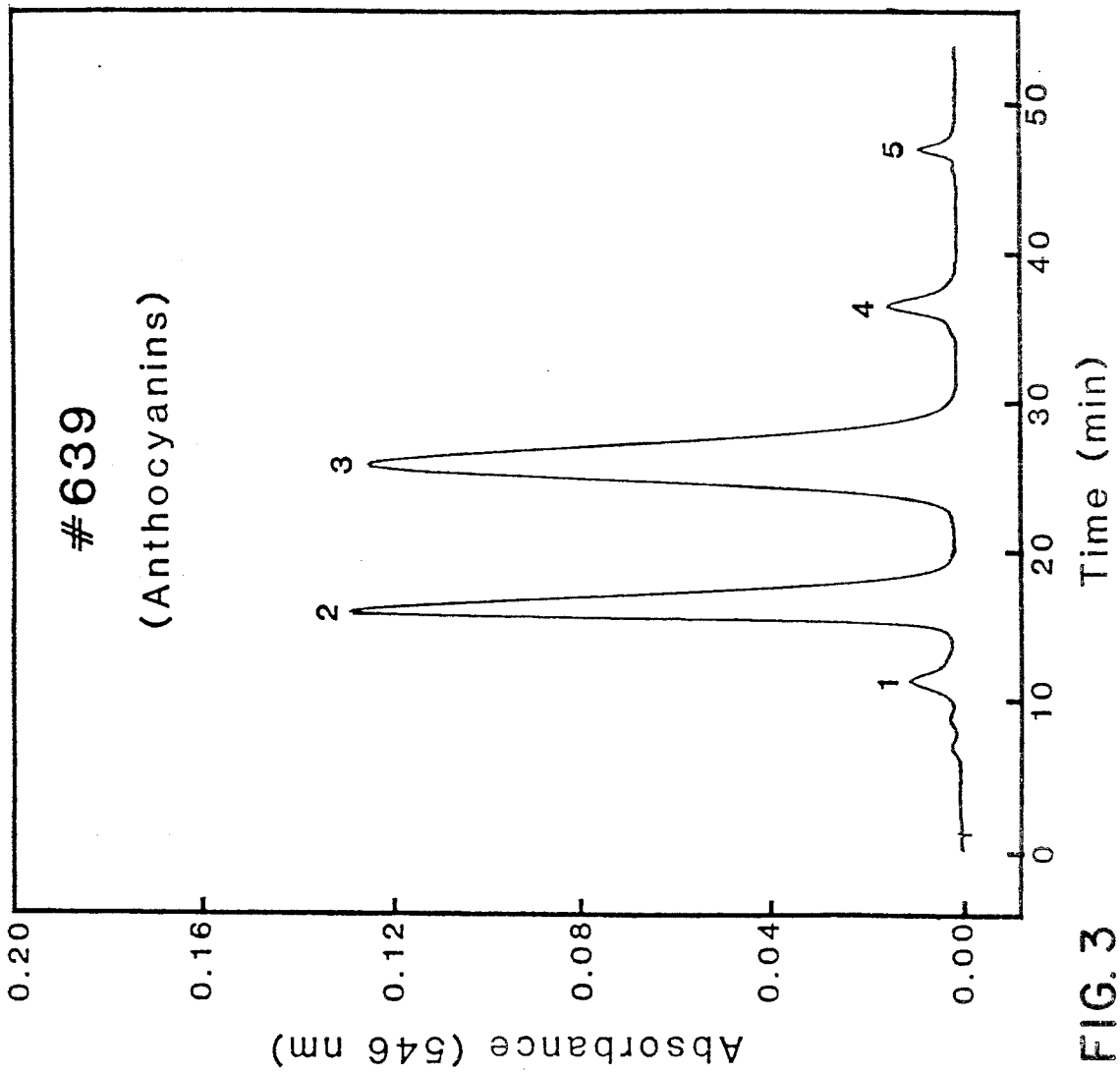
FIG. 3 is a graph of the anthocyanins fingerprinting of the new cultivar.

The new cultivar has been fingerprinted by the U.S. Department of Agriculture, Florist and Nursery Crops Laboratory, Beltsville, Md. Young plants arrived from Oglevee Floral Company of Connellsville, Pa. and were grown under standard conditions in a greenhouse at Beltsville, Md. The fingerprinting was conducted by high pressure liquid chromatographic analysis of the anthocyanin and flavonol chemical markers utilizing flower petals as an adjunct for cultivar identification. Petals were selected for analysis from individual mature flowers sampled just after anthesis. It should be noted that changes in environment can influence the biosynthesis of the flavonoids. The absorption profiles (fingerprints) are illustrated in FIG. 2 and 3.

I claim:

1. A new and distinct variety of geranium plant, substantially as herein shown and described.

* * * * *

UNITED STATES PATENT AND TRADEMARK OFFICE

CERTIFICATE OF CORRECTION

Plant
PATENT NO. : 5,311

DATED : October 30, 1984

INVENTOR(S) : Guenter Hofmann

It is certified that error appears in the above-identified patent and that said Letters Patent is hereby corrected as shown below:

Column 1 Line 31

Delete --FIG. 1 is a graph of the flavonols fingerprinting,--.

Signed and Sealed this

*Ninth* Day of *April 1985*

[SEAL]

*Attest:*

DONALD J. QUIGG

*Attesting Officer* *Acting Commissioner of Patents and Trademarks*